United States Patent
Bandman et al.

(10) Patent No.: US 6,180,342 B1
(45) Date of Patent: Jan. 30, 2001

(54) VACUOLAR PROTON ATPASE SUBUNITS

(75) Inventors: Olga Bandman, Mountain View; Y. Tom Tang, San Jose; Preeti Lal, Santa Clara; Neil C. Corley, Mountain View; Karl J. Guegler, Menlo Park; Chandra Patterson, Mountain View, all of CA (US)

(73) Assignee: Incyte Pharmaceuticals, Inc., Palo Alto, CA (US)

( * ) Notice: Under 35 U.S.C. 154(b), the term of this patent shall be extended for 0 days.

(21) Appl. No.: 09/098,789

(22) Filed: Jun. 17, 1998

(51) Int. Cl.[7] .............................. C12Q 1/68; C12P 21/06; C12N 9/14; C12N 5/22; C07H 21/04
(52) U.S. Cl. ..................... 435/6; 435/69.1; 435/91.2; 435/252.3; 435/254.11; 435/320.1; 435/325; 435/410; 435/195; 536/23.2; 536/23.5
(58) Field of Search .................................. 435/195, 252.3, 435/320.1, 6, 69.1, 254.11, 325, 410, 91.2; 536/23.2, 23.5

(56) References Cited

PUBLICATIONS

Mellman, I. et al., "Acidification of the Endocytic and Exocytic Pathways", *Ann. Rev. Biochem.*, 55: 663–700 (1986).
Wang, Y. and E. Floor, "Hydrogen Peroxide Inhibits the Vacuolar H[+]–ATPase in Brain Synaptic Vesicles at Micromolar Concentrations", *J. Neurochem.*, 70: 646–652 (1995).
Nishihara, T. et al., "Specific Inhibitors of Vacuolar Type H[+]–ATPases Induce Apoptotic Cell Death", *Biochem. Biophys. Res. Commun.*, 212: 255–262 (1995).
Niessen, H. et al., "Granulocyte Colony–Stimulating Factor Upregulates the Vacuolar Proton ATPase in Human Neutrophils", *Blood*, 90: 4598–4601 (1997).
Nelson, H. et al., "A bovine cDNA and a yeast gene (VMA8) encoding the subunit D of the vacuolar H[+]–ATPase", *Proc. Natl. Acad. Sci. USA*, 92: 497–501 (1995).
Noumi, T. et al., "Mutational analysis of yeast vacuolar H[+]–ATPase", *Proc. Natl. Acad. Sci. USA*, 88: 1938–1942 (1991).
Ludwig, J. et al., "Identication and Characterization of a Novel 9.2–kDa Membrane Sector–associated Protein of Vacuolar Proton–ATPase from Chromaffin Granules", *J. Biol. Chem.*, 273: 10939–10947 (1998).
Supekova, L. et al., "A Novel Subunit of Vacuolar H[+]–ATPase Related to the b subunit of F–ATpases", *J. Exp. Biol.*, 199:1147–1156 (1996).
Hillier et al. (Accession A399356, Aug. 12, 1997).*
Adams et al. (Accession AA324358, Apr. 20, 1997).*
Shiina et al. (Accession AB000876, Apr. 18, 1998).*

* cited by examiner

*Primary Examiner*—Elizabeth Slobodyansky
(74) *Attorney, Agent, or Firm*—Incyte Pharmaceuticals, Inc.

(57) ABSTRACT

The invention provides human vacuolar proton ATPase subunits (VATPS) and polynucleotides which identify and encode VATPS. The invention also provides expression vectors, host cells, antibodies, agonists, and antagonists. The invention also provides methods for diagnosing, treating or preventing disorders associated with expression of VATPS.

9 Claims, 9 Drawing Sheets

```
                    9              18             27             36             45             54
5' TGG GAG CCA TCT GGT ACT TTG ACA GCA TTC AAA ACA GCA TCG GCC ATA ACA ACA 63             72             81             90             99            108
   GAA ATG GCC AGT CAG TCC CAA GGT ATC CAG CAG CTT CTG CAA GCT GAG AAG CGG
       M   A   S   Q   S   Q   G   I   Q   Q   L   L   Q   A   E   K   R 117            126            135            144            153            162
   GCA GCT GAG AAG GTG GCA GAT GCC AGA AAG AGG AAG CGG CGA CTG AAG CAG
       A   A   E   K   V   A   D   A   R   K   R   K   R   R   L   K   Q 171            180            189            198            207            216
   GCA AAG GAG GAG GCA CAG ATG GAG GTG GAG CAA TAC CGC AGA GAG CGA CAC
       A   K   E   E   A   Q   M   E   V   E   Q   Y   R   R   E   R   H 225            234            243            252            261            270
   GAA TTC CAG AGC AAG CAG CAG CAG GCG GCC ATG TCC CAG GGG AAC CTG TCT GCT
       E   F   Q   S   K   Q   Q   Q   A   A   M   S   Q   G   N   L   S   A 279            288            297            306            315            324
   GAG GAG CAG CAG ACA AGG CGC CAG CAG GTG CAG GCC ATG CAG GGC ATG CAG TCC CAG CAG
       E   E   Q   Q   T   R   R   Q   Q   V   Q   A   M   Q   G   M   Q   S   Q   Q 333            342            351            360            369            378
   AGA CGA GAG CGT GTC CTG GCC CAG CTT CTT GGC ATG GTC TGC GAC GTC AGG
       R   R   E   R   V   L   A   Q   L   L   G   M   V   C   D   V   R

FIGURE 1A
```

```
387         396         405         414         423         432
CCC CAG GTC CAC CCC AAC TAC CGG ATT TCT GCC TAG GGC CAC CGT AGG GCC TGA
 P   Q   V   H   P   N   Y   R   I   S   A 441         450         459         468         477         486
CTC CTT CCA GTT CCC TCC CTC AAA GAA ATC CTC CAA TCA AAA TCA CCT CCC 495         504         513         522         531         540
ACC ATA ATC CCT GTC TTC TTT CCA TCC CCT AGA AAT CCT GGG AGG CAG GAT CCA 549         558         567         576         585         594
ATA ATT TTC CTG TGA CAC TTA TAA ATA TCC TGC TCA CAT CTG AAT CTC CTT GTT 603         612         621         630         639         648
GTT CTT TAA CCC TCA CTG GGA CTT TGT AAA CTT CCA AGT CAT TCT CAC CTA AAC 657         666         675         684         693         702
CCT CTG TGA AAT TTG TAA TAT GGG GAA GTA GGA ATG TGG AAA ACA TCC TGA CTT 711         720         729         738         747         756
CAG TGT CTG GCC GAT GTG GGT CCC TCT CTT GAC GTC ACT GTC TGC TGG CTG TGA 765         774         783         792         801         810
AAC GAC AAG CTA CTT AAC TTG GTA GCC TCG ATG TCC TCC TCT GTG AAA CTG 819         828         837         846         855         864
GGA TGA TAA TGC CTA CCT TGT GAG GGT TGC TTC AAT GAT TAG GAA TCA TTC
```

FIGURE 1B

```
       873  882  891  900  909  918
TGT AAA GTC TAG CAG AGT TCC TTG CAT GTT GTA GCA GTG ATT CAG TAA GTA GCA
       927  936  945  954  963  972
ACC CTG TGA TAC TAT TAC CAC CAC CTG CTC ACT GGT CAA AAC CTA CAC AGC TGT
       981  990  999 1008 1017 1026
TTC CTC ACG TCC ATC ACT GGC TCT CTA ATT CCA CTT GTT CAT TCT GTG ACC CTA
      1035 1044 1053 1062 1071 1080
GTT ATT TTC TGA AAA ATT GGT TCT TCT CTT TTC CCA GAG ACC TTC TGA TCT CCA
      1089 1098 1107 1116 1125 1134
AAA AGA GGA GAT GAC TAC ATT TAG CCC CTC TCT TAT AAT TCC AGG TAG ATA ACT
      1143 1152 1161 1170 1179 1188
GCA TTT TGT AGC CTC TCT TTG TTT TTC TTT TGC TGA TCT TTG TCT TTA TTA GAT

TTT C 3'
```

```
                10              19              28              37              46              55
5' GGC   TGG   GGA   CCC   GCG   CAC   CTG   CAG   CGC   CCG   CTG   CTC   GGC   CCT   GCA   TCC   TGC   CTG 64              73              82              91             100             109
   GGC   ATC   CTG   CGC   CCG   GCC   ATG   ACG   GCG   CAC   TCA   TTC   GCC   CTC   CCG   GTC   ATC   ATC
                              M     T     A     H     S     F     A     L     P     V     I     I 118             127             136             145             154             163
   TTC   ACG   TTC   TGG   GGC   CTC   GTC   GGC   ATC   GCC   GGG   CCC   TGG   TTC   GTG   CCG   AAG
    F     T     F     W     G     L     V     G     I     A     G     P     W     F     V     P     K 172             181             190             199             208             217
   GGA   CCC   AAC   CGC   GGA   GTG   ATC   ATC   ACC   ATG   CTG   GTC   GCC   ACC   GCC   GTC   TGC   TGT
    G     P     N     R     G     V     I     I     T     M     L     V     A     T     A     V     C     C 226             235             244             253             262             271
   TAC   CTC   TTC   TGG   CTC   ATC   GCC   ATC   CTG   GCG   CAG   AAC   CCC   CTG   TTC   GGG   CCC
    Y     L     F     W     L     I     A     I     L     A     Q     N     P     L     F     G     P 280             289             298             307             316             325
   CAG   CTG   AAG   AAT   GAG   ACC   ATC   TGG   TAC   GTG   CGC   TTC   CTG   TGG   GAG   TGA   CCC   GCC
    Q     L     K     N     E     T     I     W     Y     V     R     F     L     W     E 334             343             352             361             370             379
   GCC   CCC   GAC   CCA   GGT   GCC   CAG   CTC   TCG   GAA   TGA   CTG   TGG   CTC   CAC   TGT   CCC   TGA 388             397             406             415             424             433
   CAA   CCC   CTT   CGT   CCG   GAC   CCT   CCC   CCA   CAC   AAC   TAT   GTC   TGG   TCA   CCA   GCT   CCC
```

FIGURE 3A

```
       442 451 460 469 478 487
TCC TGC TGG CAC CCA GAG ACC CGC AGG ACC CGG TTC CTG GAA GTC
       496 505 514 523 532 541
TTC CCA GTC TTC CCA GCC AGC CCG GGC CCT GGG GAG CCC TGG GCA CAG CAG CGG
       550 559 568 577 586 595
CCG AGG GGA TGT CCT GCT CCA ATA CCC GCA CTG CTC TGG AGT TTG CCC TCT TTC
       604 613 622 631 640 649
CCA AGG AGA TGC TGC TGG GGA GCT CAG CCC GGG GTC TTT CCC TTT ACA GAC
       658 667 676 685 694 703
GGG GCA GAT GCC AGG ACT CAG CCC ATC CTG AGG ACA CGT GTC CTC ATG GAG
       712 721 730 739 748 757
AGG GTC CTC CGG CCC AGG CGG GGG AGT CGG TGC CCA GTC AGC TCT GCC ACC
       766 775 784 793 802 811
ATC CTG CTG GGA ACT GGG GGG GCC TCT ATT GGG TTA TAG GCA AGG CCT TTT CTC
       820 829 838 847 856 865
TGG CAT GGA ATT GTT AAT TTT CTG ACA CGT CTA GAT GTG AAA TTT CTG AAA ATG
       874 883 892 901 910 919
TTG AAG CAG AGA AAC ATT CAC ACA CAA AAA GCA TAG TCA TGT GGG TCC AGA
       928 937 946 955 964 973
TGG CCT CAG TCC TAG ATG TTG GCA CCC TTT GCT GTG TCT CCT CAG AGT ATC CTG
```

FIGURE 3B

```
      982         991        1000        1009        1018        1027
TTC CGC CTC CTG CCA CCT GGA CCT CCC TCA GTG GAT GTC TTC CCT CCC CCG ACC 1036        1045        1054        1063        1072        1081
CCA GCC TGT CAG TCC GAG CAC AGT GCA GGT TTG GCT CTG ACT TGG GCC TTT GGC 1090        1099        1108        1117        1126        1135
TGC AGT GGG GGT GGA TTT CAG AGC CTC TCA TGG CAG CAT CTA AGT GAC CAG AGC 1144        1153        1162        1171        1180        1189
TGG GAT GAG AGA GGG GAA GGG GCA ATG TGA GTG GCG CTA TGG GAC GGG CCA GCC 1198        1207        1216        1225        1234        1243
CTG CTC CTG AGC CAG CCC CGC CCT CTG CCC CCT GGC CCT GGG CTC TGT GCT AGG 1252        1261        1270        1279        1288        1297
GAT GGT GAA GAA TGG GGG CGT GCC AGC CTG GCA GGA GTG GGA AGC AAC ACG CAG 1306        1315        1324        1333        1342        1351
GGG TCC CGG ACC TCT CCA GCC TTG CCC TCA CGC TTA TCC GAG CTC CCA GTG TGG 1360        1369        1378        1387        1396        1405
TTA GCA CAG AGC TCA CCC ACC TTG CCT GGC TCC CAG CTG GGG CCT GTC CTC ACT 1414        1423        1432        1441        1450        1459
GGT GCT CCA GGG GAA GAA ACG ACA GCC TCA CTT CTG TAT GGA CTG CTG ATG TGG 1468        1477        1486        1495        1504        1513
CCT GCC ATC CTG TTC AGC GGG CAT TGT CTT TGG AGC AGG AGA ATA GGA TGC
```

FIGURE 3C

```
     1522          1531          1540          1549          1558          1567
CTC TCA CTC ACA TGC CAG TTC CTG GCT GGC CAG CTG CTC AGG GCT CAG GCT GGG 1576          1585          1594          1603          1612          1621
GCC TCC CAT TGA CAT CCT CCC CCT ACA CTC CCT CTC TGA GCC TCC GTC GCC CCT 1630          1639          1648          1657          1666          1675
CCT GTT GGG TAA GGG TGT TGA GTG TGA CTT GTG CTG AAA ACC TGG TTC ATA TAT

1684
AAT AAA TAA A 3'
```

VACUOLAR PROTON ATPASE SUBUNITS

FIELD OF THE INVENTION

This invention relates to nucleic acid and amino acid sequences of vacuolar proton ATPase subunits and to the use of these sequences in the diagnosis, treatment, and prevention of cell proliferative and neurological disorders.

BACKGROUND OF THE INVENTION

Proton-translocating adenosine triphosphatases (proton ATPases) are a large class of membrane-proteins that use the energy of ATP hydrolysis to generate an electrochemical proton gradient across a membrane. The resultant gradient may be used to transport other ions across the membrane ($Na^+$, $K^+$, or $Cl^-$) or to maintain an acidic environment important to the function of many cellular vesicles (Mellman, I. et al. (1986) Ann. Rev. Biochem. 55:663–700). Proton ATPases are further subdivided into the mitochondrial F-ATPases, the plasma membrane ATPases, and the vacuolar ATPases.

The vacuolar proton ATPases (vp-ATPases) provide most of the energy required for transport processes in the vacuolar system in eukaryotic cells. vp-ATPases establish and maintain an acidic pH within various vesicles involved in the processes of endocytosis and exocytosis. Such vesicles include phagosomes, lysosomes, endosomes, and secretory vesicles. Endocytosis is the process in cells of internalizing nutrients, solutes or small particles (pinocytosis), or large particles such as internalized receptors, viruses, bacteria, or bacterial toxins (phagocytosis). Exocytosis is the process of transporting molecules to the cell surface. Exocytosis facilitates the placement or localization of membrane-bound receptors or other membrane proteins and the secretion of hormones, neurotransmitters, digestive enzymes, and wastes. Endocytosis and exocytosis are fundamental to the function of all types of cells.

Alterations in both endocytosis and exocytosis play a role in a variety of disorders. For example, synaptic vesicles play a major role in neural transmission at nerve terminals through storage and controlled release of neurotransmitters. Neurotransmitter uptake into synaptic vesicles is driven by the electrochemical proton gradient generated by vp-ATPase. Inactivation of vp-ATPase has been shown to inhibit glutamate uptake by synaptic vesicles, decreasing neurotransmitter release during episodes of oxidative stress or in response to second messenger signaling. Additionally, inactivation of vp-ATPase has been shown to trigger apoptosis in a variety of immortalized and primary cell lines. Activation of vp-ATPases has been found to delay apoptosis (Wang, Y. et al. (1998) J. Neurochem. 70:646–652; Nishihara, T. et al. (1995) Biochem. Biophys. Res. Commun. 212: 255–262; and Niessen, H. et al. (1997) Blood 90: 4598–4601.)

The vp-ATPases and the F-ATPases, which function in ATP synthesis and hydrolysis in mitochondria, are related in both their subunit structure and evolutionary origin. Both contain distinct catalytic and membrane sectors, and each sector contains multiple subunits. The catalytic sector of vp-ATPase consists of five subunits designated A (72 kDa), B (57 kDa), C (41 kDa), D (34 kDa), and E (33 kDa) (Nelson, H. et al. (1995) Proc. Natl. Acad. Sci. 92:497–501). Three subunits, AC115, AC39, and a proteolipid component, have been identified in the membrane sector of vp-ATPase from various sources. The proteolipid subunit has been implicated in the mechanism of energy transfer in the enzyme. The membrane sector has several functions including proton conduction across the membrane, energy coupling with the catalytic sector, communication with the lumen, and modulation of enzyme activity. Mutational studies in yeast have shown that, while the membrane sector may be assembled independently of the catalytic sector, assembly of the catalytic sector is absolutely dependent on previous assembly of the membrane sector (Noumi, T. et al. (1991) Proc. Natl. Acad. Sci. 88: 1938–42; Ludwig, J. et al. (1998) J. Biol. Chem. 273: 10939–10947; and Supekova, L. et al. (1996)199:1147–1156). Thus, expression and assembly of the membrane sector subunits control the overall activity of the enzyme complex.

The discovery of new vacuolar proton ATPase subunits and the polynucleotides encoding them satisfies a need in the art by providing new compositions which are useful in the diagnosis, prevention, and treatment of cell proliferative and neurological disorders.

SUMMARY OF THE INVENTION

The invention features substantially purified polypeptides, vacuolar proton ATPase subunits, referred to collectively as "VATPS" and individually as "VATPS-1" and "VATPS-2." In one aspect, the invention provides a substantially purified polypeptide comprising an amino acid sequence selected from the group consisting of SEQ ID NO: 1, SEQ ID NO: 2, a fragment of SEQ ID NO: 1, and a fragment of SEQ ID NO: 2.

The invention further provides a substantially purified variant having at least 90% amino acid identity to the amino acid sequences of SEQ ID NO: 1 or SEQ ID NO: 2, or to a fragment of either of these sequences. The invention also provides an isolated and purified polynucleotide encoding the polypeptide comprising an amino acid sequence selected from the group consisting of SEQ ID NO: 1, SEQ ID NO: 2, a fragment of SEQ ID NO: 1, and a fragment of SEQ ID NO: 2. The invention also includes an isolated and purified polynucleotide variant having at least 70% polynucleotide sequence identity to the polynucleotide encoding the polypeptide comprising an amino acid sequence selected from the group consisting of SEQ ID NO: 1, SEQ ID NO: 2, a fragment of SEQ ID NO: 1, and a fragment of SEQ ID NO: 2.

Additionally, the invention provides an isolated and purified polynucleotide which hybridizes under stringent conditions to the polynucleotide encoding the polypeptide comprising an amino acid sequence selected from the group consisting of SEQ ID NO: 1, SEQ ID NO: 2, a fragment of SEQ ID NO: 1 and a fragment of SEQ ID NO: 2, as well as an isolated and purified polynucleotide having a sequence which is complementary to the polynucleotide encoding the polypeptide comprising the amino acid sequence selected from the group consisting of SEQ ID NO: 1, SEQ ID NO: 2, a fragment of SEQ ID NO: 1, and a fragment of SEQ ID NO: 2.

The invention also provides an isolated and purified polynucleotide comprising a polynucleotide sequence selected from the group consisting of SEQ ID NO: 3, SEQ ID NO: 4, a fragment of SEQ ID NO:

and a fragment of SEQ ID NO: 4. The invention further provides an isolated and purified polynucleotide variant having at least 70% polynucleotide sequence identity to the polynucleotide sequence comprising a polynucleotide sequence selected from the group consisting of SEQ ID NO: 3, SEQ ID NO: 4, a fragment of SEQ ID NO: 3, and a fragment of SEQ ID NO: 4, as well as an isolated and purified polynucleotide having a sequence which is complementary to the polynucleotide comprising a polynucleotide sequence selected from the group consisting of SEQ ID NO: 3, SEQ ID NO: 4, a fragment of SEQ ID NO: 3, and a fragment of SEQ ID NO: 4.

The invention further provides an expression vector containing at least a fragment of the polynucleotide encoding the polypeptide comprising an amino acid sequence selected from the group consisting of SEQ ID NO: 1, SEQ ID NO: 2, a fragment of SEQ ID NO: 1, and a fragment of SEQ ID NO: 2. In another aspect, the expression vector is contained within a host cell.

The invention also provides a method for producing a polypeptide comprising the amino acid sequence selected from the group consisting of SEQ ID NO: 1, SEQ ID NO: 2, a fragment of SEQ ID NO: 1, and a fragment of SEQ ID NO: 2, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO: 1, SEQ ID NO: 2, a fragment of SEQ ID NO: 1, and a fragment of SEQ ID NO: 2 in conjunction with a suitable pharmaceutical carrier.

The invention further includes a purified antibody which binds to a polypeptide comprising the amino acid sequence selected from the group consisting of SEQ ID NO: 1, SEQ ID NO: 2, a fragment of SEQ ID NO: 1, and a fragment of SEQ ID NO: 2, as well as a purified agonist and a purified antagonist to the polypeptide.

The invention also provides a method for treating or preventing a neurological disorder associated with reduced expression or activity of VATPS, the method comprising administering to a subject in need of such treatment an effective amount of a pharmaceutical composition comprising a substantially purified polypeptide having the amino acid sequence selected from the group consisting of SEQ ID NO: 1 through 5, and fragments thereof in conjunction with a suitable pharmaceutical carrier.

The invention also provides a method for treating or preventing a neurological disorder associated with increased expression or activity of VATPS, the method comprising administering to a subject in need of such treatment an effective amount of an antagonist of the polypeptide having an amino acid sequence selected from the group consisting of SEQ ID NO: 1, SEQ ID NO: 2, a fragment of SEQ ID NO: 1, and a fragment of SEQ ID NO: 2.

The invention also provides a method for treating or preventing a cell proliferative disorder associated with reduced expression or activity of VATPS, the method comprising administering to a subject in need of such treatment an effective amount of a pharmaceutical composition comprising a substantially purified polypeptide having the amino acid sequence selected from the group consisting of SEQ ID NO: 1 through 5, and fragments thereof in conjunction with a suitable pharmaceutical carrier.

The invention also provides a method for treating or preventing a cell proliferative disorder associated with increased expression or activity of VATPS, the method comprising administering to a subject in need of such treatment an effective amount of an antagonist of the polypeptide having an amino acid sequence selected from the group consisting of SEQ ID NO: 1, SEQ ID NO: 2, a fragment of SEQ ID NO: 1, and a fragment of SEQ ID NO: 2.

The invention also provides a method for detecting a polynucleotide encoding the polypeptide comprising the amino acid sequence selected from the group consisting of SEQ ID NO: 1, SEQ ID NO: 2, a fragment of SEQ ID NO: 1, and a fragment of SEQ ID NO: 2 in a biological sample containing nucleic acids, the method comprising the steps of: (a) hybridizing the complement of the polynucleotide sequence encoding the polypeptide comprising the amino acid sequence selected from the group consisting of SEQ ID NO: 1, SEQ ID NO: 2, a fragment of SEQ ID NO: 1, and a fragment of SEQ ID NO: 2 to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the method further comprises amplifying the polynucleotide prior to hybridization.

BRIEF DESCRIPTION OF THE FIGURES AND TABLES

FIGS. 1A, 1B, and 1C show the amino acid sequence (SEQ ID NO: 1) and nucleic acid sequence (SEQ ID NO: 3) of VATPS-1. The alignment was produced using MacDNA-SIS PRO™ software (Hitachi Software Engineering Co. Ltd., San Bruno, Calif.).

FIG. 2 shows the amino acid sequence alignments between VATPS-1 (Incyte Clone number 2246348; SEQ ID NO: 1) and bovine vacuolar ATPase subunit (GI 1699359; SEQ ID NO: 14), produced using the multisequence alignment program of LASERGENE™ software (DNASTAR Inc, Madison Wis.).

FIGS. 3A, 3B, 3C and 3D show the amino acid sequence (SEQ ID NO: 2) and nucleic acid sequence (SEQ ID NO: 4) of VATPS-2. The alignment was produced using MacDNA-SIS PRO™ software.

FIG. 4 shows the amino acid sequence alignments between VATPS-2 (Incyte Clone number 2246348; SEQ ID NO: 2) and human vacuolar ATPase subunit (GI 2584789; SEQ ID NO: 15), produced using the multisequence alignment program of LASERGENE™ software.

TABLE 1 describes the programs, algorithms, databases, and scores for analyzing VATPS.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"VATPS" refers to the amino acid sequences of substantially purified VATPS obtained from any species, particularly a mammalian species, including bovine, ovine, porcine, murine, equine, and preferably the human species, from any source, whether natural, synthetic, semi-synthetic, or recombinant.

The term "agonist" refers to a molecule which, when bound to VATPS, increases or prolongs the duration of the effect of VATPS. Agonists may include proteins, nucleic acids, carbohydrates, or any other molecules which bind to and modulate the effect of VATPS.

An "allelic variant" is an alternative form of the gene encoding VATPS. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding VATPS include those sequences with deletions, insertions, or substitutions of different nucleotides, resulting in a polynucleotide the same as VATPS or a polypeptide with at least one functional characteristic of VATPS. Included within this definition are polymorphisms which may or may not be readily detectable using a particular oligonucleotide probe of the polynucleotide encoding VATPS, and improper or unexpected hybridization to allelic variants, with a locus other than the normal chromosomal locus for the polynucleotide sequence encoding VATPS. The encoded protein may also be "altered," and may contain deletions, insertions, or substitutions of amino acid residues which produce a silent change and result in a functionally equivalent VATPS. Deliberate amino acid substitutions may be made on the basis of similarity in polarity, charge, solubility, hydrophobicity, hydrophilicity, and/or the amphipathic nature of the residues, as long as the biological or immunological activity of VATPS is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence" refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of VATPS which are preferably at least 5 to about 15 amino acids in length, most preferably at least 14 amino acids, and which retain some biological activity or immunological activity of VATPS. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which, when bound to VATPS, decreases the amount or the duration of the effect of the biological or immunological activity of VATPS. Antagonists may include proteins, nucleic acids, carbohydrates, antibodies, or any other molecules which decrease the effect of VATPS.

The term "antibody" refers to intact molecules as well as to fragments thereof, such as Fab, F(ab')$_2$, and Fv fragments, which are capable of binding the epitopic determinant. Antibodies that bind VATPS polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The term "biologically active," refers to a protein having structural, regulatory, or biochemical functions of a naturally occurring molecule. Likewise, "immunologically active" refers to the capability of the natural, recombinant, or synthetic VATPS, or of any oligopeptide thereof, to induce a specific immune response in appropriate animals or cells and to bind with specific antibodies.

The terms "complementary" or "complementarity" refer to the natural binding of polynucleotides by base pairing. For example, the sequence "5' A-G-T 3'" binds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence" refer broadly to any composition containing the given polynucleotide or amino acid sequence. The composition may comprise a dry formulation or an aqueous solution. Compositions comprising polynucleotide sequences encoding VATPS or fragments of VATPS may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g., sodium dodecyl sulfate (SDS), and other components, e.g., Denhardt's solution, dry milk, salmon sperm DNA, etc.

"Consensus sequence" refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GELVIEW™ Fragment Assembly system (GCG, Madison, Wis.). Some sequences have been both extended and assembled to produce the consensus sequence.

The term "correlates with expression of a polynucleotide" indicates that the detection of the presence of nucleic acids, the same or related to a nucleic acid sequence encoding VATPS, by Northern analysis is indicative of the presence of nucleic acids encoding VATPS in a sample, and thereby correlates with expression of the transcript from the polynucleotide encoding VATPS.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity" refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign™ program (DNASTAR, Inc., Madison WI). The MegAlign™ program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid binds with a complementary strand through base pairing.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition" refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray" refers to an arrangement of distinct polynucleotides arrayed on a substrate, e.g., paper, nylon or any other type of membrane, filter, chip, glass slide, or any other suitable solid support.

The terms "element" or "array element" in a microarray context, refer to hybridizable polynucleotides arranged on the surface of a substrate.

The term "modulate" refers to a change in the activity of VATPS. For example, modulation may cause an increase or a decrease in protein activity, binding characteristics, or any other biological, functional, or immunological properties of VATPS.

The phrases "nucleic acid" or "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked" refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. "Oligonucleotide" is substantially equivalent to the terms "amplimer," "primer," "oligomer," and "probe," as these terms are commonly defined in the art. "Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

The term "sample" is used in its broadest sense. A biological sample suspected of containing nucleic acids encoding VATPS, or fragments thereof, or VATPS itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

The terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of VATPS polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE™ software.

The term "variant," when used in the context of a polynucleotide sequence, may encompass a polynucleotide sequence related to VATPS. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

The Invention

The invention is based on the discovery of a new human vacuolar proton ATPase subunits (VATPS), the polynucleotides encoding VATPS, and the use of these compositions for the diagnosis, treatment, or prevention of cell proliferative and neurological disorders.

Nucleic acids encoding the VATPS-1 of the present invention were first identified in Incyte Clone 2246348 from the hippocampus cDNA library (HIPONON02) using a computer search, e.g., BLAST, for amino acid sequence alignments. A consensus sequence, SEQ ID NO: 3, was derived from the following overlapping and/or extended nucleic acid sequences: Incyte Clones 2246348CT1 (HIPONON02), and 659609HI (BRAINOT03).

In one embodiment, the invention encompasses a polypeptide comprising the amino acid sequence of SEQ ID NO: 1, as shown in FIGS. 1A, 1B, and 1C. VATPS-1 is 118 amino acids in length and has a potential N-glycosylation site at residue N68 and a potential protein kinase C phosphorylation site at residue T77. As shown in FIG. 2, VATPS-1 has chemical and structural similarity with bovine vacuolar ATPase subunit (GI 1699359; SEQ ID NO: 14). In particular, VATPS-1 and bovine vacuolar proton ATPase subunit share 69% identity. Northern analysis shows the expression of this sequence in various libraries, at least 58% of which involve neurological disorders and at least 36% are immortalized or cancerous. Of particular note is the expression of VATPS-1 in neural tissues.

Nucleic acids encoding the VATPS-2 of the present invention were first identified in Incyte Clone from the testicular tumor cDNA library (TESTTUT02) using a computer search, e.g., BLAST, for amino acid sequence alignments. A consensus sequence, SEQ ID NO: 4, was derived from the following overlapping and/or extended nucleic acid sequences: Incyte Clones 2346304H1 (TESTTUT02), 1616336T6 (BRAITUT12), 1661631F6 (BRSTNOT09), 1811952F6 (PROSTUT12), 2155351T6 (BRAINOT09), 2481208H1 (SMCANOT01), and 3110132F6 (BRSTTUT15).

In one embodiment, the invention encompasses a polypeptide comprising the amino acid sequence of SEQ ID NO: 2, as shown in FIGS. 3A, 3B, 3C and 3D. VATPS-2 is 81 amino acids in length and has a potential N-glycosylation site at residue N70. As shown in FIG. 4, VATPS-2 has chemical and structural similarity with human vacuolar proton ATPase subunit (GI 2584789; SEQ ID NO: 15). In particular, VATPS-2 and human vacuolar proton ATPase subunit share 70% identity. Northern analysis shows the expression of this sequence in various libraries, at least 58% of which are immortalized or cancerous and at least 22% of which involve an immune response. Of particular note is the expression of VATPS-2 in neural tissues.

The invention also encompasses VATPS variants. A preferred VATPS variant is one which has at least about 80%, more preferably at least about 90%, and most preferably at least about 95% amino acid sequence identity to the VATPS amino acid sequence, and which contains at least one functional or structural characteristic of VATPS.

The invention also encompasses polynucleotides which encode VATPS. In a particular embodiment, the invention encompasses a polynucleotide sequence selected from the group consisting of SEQ ID NO: 3, SEQ ID NO: 4, a fragment of SEQ ID NO: 3, and a fragment of SEQ ID NO: 4.

The invention also encompasses a variant of a polynucleotide sequence encoding VATPS. In particular, such a variant polynucleotide sequence will have at least about 70%, more preferably at least about 80%, and most preferably at least about 95% polynucleotide sequence identity to the polynucleotide sequence encoding VATPS. A particular aspect of the invention encompasses a variant of a nucleic acid sequence selected from the group consisting of SEQ ID NO: 3, SEQ ID NO: 4, a fragment of SEQ ID NO: 3 and a fragment of SEQ ID NO: 4 which has at least about 70%, more preferably at least about 80%, and most preferably at least about 95% polynucleotide sequence identity to a nucleic acid sequence selected from the group consisting of SEQ ID NO: 3, SEQ ID NO: 4, a fragment of SEQ ID NO: 3, and a fragment of SEQ ID NO: 4. Any one of the polynucleotide variants described above can encode an amino acid sequence which contains at least one functional or structural characteristic of VATPS.

It will be appreciated by those skilled in the art that as a result of the degeneracy of the genetic code, a multitude of polynucleotide sequences encoding VATPS, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring VATPS, and all such variations are to be considered as being specifically disclosed.

Although nucleotide sequences which encode VATPS and its variants are preferably capable of hybridizing to the nucleotide sequence of the naturally occurring VATPS under appropriately selected conditions of stringency, it may be advantageous to produce nucleotide sequences encoding VATPS or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding VATPS and its derivatives without altering the encoded amino acid sequences include the production of RNA transcripts having more desirable properties, such as a greater half-life, than transcripts produced from the naturally occurring sequence.

The invention also encompasses production of DNA sequences which encode VATPS and VATPS derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding VATPS or any fragment thereof.

Also encompassed by the invention are polynucleotide sequences that are capable of hybridizing to the claimed polynucleotide sequences, and, in particular, to those shown in SEQ ID NO: 3, SEQ ID NO: 4, or a fragment of SEQ ID NO: 3, or a fragment of SEQ ID NO: 4 under various conditions of stringency. (See e.g., Wahl, G. M. and S. L. Berger (1987) Methods Enzymol. 152:399–407; Kimmel, A. R. (1987) Methods Enzymol. 152:507–51 1.)

Methods for DNA sequencing are well known in the art and may be used to practice any of the embodiments of the invention. The methods may employ such enzymes as the Klenow fragment of DNA polymerase I, SEQUENASE(3 (US Biochemical Corp., Cleveland, Ohio), Taq polymerase (Perkin Elmer), thermostable T7 polymerase (Amersham Pharmacia Biotech, Piscataway, N.J.), or combinations of polymerases and proofreading exonucleases such as those found in the ELONGASE amplification system (Life Technologies, Gaithersburg Md.). Preferably, sequence preparation is automated with machines such as the Hamilton MICROLAB 2200 (Hamilton, Reno, Nev.), Peltier Thermal Cycler (PTC200; MJ Research Watertown, Mass.) and the ABI CATALYST 800 (Perkin Elmer). Sequencing is then carried out using either ABI 373 or 377 DNA Sequencing Systems (Perkin Elmer) or capillary electrophoresis (Molecular Dynamics). The resulting sequences are analyzed using a variety of algorithms which are well known in the art. (See, e.g., Ausubel, supra, ch. 7.7; and Meyers, R. A. (1995) *Molecular Biology and Biotechnology*, Wiley VCH, Inc., New York, N.Y., pp. 856–853.)

The nucleic acid sequences encoding VATPS may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–1 19.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PromoterFinder™ libraries to walk genomic DNA (Clontech, Palo Alto, Calif.). This procedure avoids the need to screen libraries and is useful in finding intron/exon junctions. For all PCR-based methods, primers may be designed using commercially available software, such as OLIGO™ 4.06 Primer Analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode VATPS may be cloned in recombinant DNA molecules that direct expression of VATPS, or fragments or functional equivalents thereof, in appropriate host cells. Due to the inherent degeneracy of the genetic code, other DNA sequences which encode substantially the same or a functionally equivalent amino acid sequence may be produced and used to express VATPS.

The nucleotide sequences of the present invention can be engineered using methods generally known in the art in order to alter VATPS-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding VATPS may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, VATPS itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431A Peptide Synthesizer (Perkin Elmer). Additionally, the amino acid sequence of VATPS, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, WH Freeman and Co., New York, N.Y.)

In order to express a biologically active VATPS, the nucleotide sequences encoding VATPS or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding VATPS. Such elements may vary in their strength and specificity. Specific initiation signals may also be used to achieve more efficient translation of sequences encoding VATPS. Such signals include the ATG initiation codon and adjacent sequences, e.g. the Kozak sequence. In cases where sequences encoding VATPS and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding VATPS and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et at. (1995, and periodic supplements) Current Protocols in Molecular Biology, John Wiley & Sons, New York, N.Y., ch. 9, 13, and 16.)

A variety of expression vector/host systems may be utilized to contain and express sequences encoding VATPS. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding VATPS. For example, routine cloning, subcloning, and propagation of polynucleotide sequences encoding VATPS can be achieved using a multifunctional *E. coli* vector such as Bluescript(D (Stratagene) or pSport1™ plasmid (Life Technologies). Ligation of sequences encoding VATPS into the vector's multiple cloning site disrupts the lacZ gene, allowing a calorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of VATPS are needed, e.g. for the production of antibodies, vectors which direct high level expression of VATPS may be used. For example, vectors containing the strong, inducible T5 or T7 bacteriophage promoter may be used.

Yeast expression systems may be used for production of VATPS. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of VATPS. Transcription of sequences encoding VATPS may be driven viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be used.

(See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding VATPS may be ligated into an adenovirus transcription/translation complex consisting of the late promoter and tripartite leader sequence. Insertion in a non-essential E1 or E3 region of the viral genome may be used to obtain infective virus which expresses VATPS in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of VATPS in cell lines is preferred. For example, sequences encoding VATPS can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻ cells, respectively. (See, e.g., Wigler, M. et al. (1977) Cell 11 :223–232; and Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP) (Clontech, Palo Alto, Calif.), β glucuronidase and its substrate β-D-glucuronoside, or luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding VATPS is inserted within a marker gene sequence, transformed cells containing sequences encoding VATPS can be identified by the absence of marker gene function. Alternatively, a marker gene can be placed in tandem with a sequence encoding VATPS under the control of a single promoter. Expression of the marker gene in response to induction or selection usually indicates expression of the tandem gene as well.

In general, host cells that contain the nucleic acid sequence encoding VATPS and that express VATPS may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of VATPS using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on VATPS is preferred, but a competitive binding assay may be employed. These and other assays are well known in the art. (See, e.g., Hampton, R. et al. (1990) *Serological Methods, a Laboratory Manual*, APS Press, St Paul, Minn., Section IV; Coligan, J. E. et al. (1997 and periodic supplements) *Current Protocols in Immunology*, Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding VATPS include oligolabeling, nick translation, end-labeling, or PCR amplification using a labeled nucleotide. Alternatively, the sequences encoding VATPS, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding VATPS may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode VATPS may be designed to contain signal sequences which direct secretion of VATPS through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

In another embodiment of the invention, natural, modified, or recombinant nucleic acid sequences encoding VATPS may be ligated to a heterologous sequence resulting in translation of a fusion protein in any of the aforementioned host systems. For example, a chimeric VATPS protein containing a heterologous moiety that can be recognized by a commercially available antibody may facilitate the screening of peptide libraries for inhibitors of VATPS activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the VATPS encoding sequence and the heterologous protein sequence, so that VATPS may be cleaved away from the heterologous moiety following purification. Methods for fusion protein expression and purification are discussed in Ausubel, F. M. et al. (1995 and periodic supplements) *Current Protocols in Molecular Biology*, John Wiley & Sons, New York, N.Y., ch 10. A variety of commercially available kits may also be used to facilitate expression and purification of fusion proteins.

In a further embodiment of the invention, synthesis of radiolabeled VATPS may be achieved in vitro using the TNT™ rabbit reticulocyte lysate or wheat germ extract systems (Promega, Madison, Wis.).

These systems couple transcription and translation of protein-coding sequences operably associated with the T7, T3, or SP6 promoters. Translation takes place in the presence of a radiolabeled amino acid precursor, preferably $^{35}$S-methionine.

Fragments of VATPS may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431 A Peptide Synthesizer (Perkin Elmer). Various fragments of VATPS may be synthesized separately and then combined to produce the full length molecule.

Therapeutics

Chemical and structural similarity, e.g., in the context of sequences and motifs, exists between VATPS-1 and bovine vacuolar ATPase subunit (GI 1699359), and between VATPS-2 and human vacuolar ATPase subunit (GI 2584789). In addition, the expression of VATPS is closely associated with cell proliferation and neural tissues. Therefore, in cell proliferative and neurological disorders where VATPS is an activator, or enhancer, and is promoting cell proliferative and neurological disorders, it is desirable to decrease the expression of VATPS. In cell proliferative and neurological disorders where VATPS is an inhibitor, or suppressor of cell proliferative and neurological disorders, it is desirable to increase the expression of VATPS.

Therefore, in one embodiment, VATPS or a fragment or derivative thereof may be administered to a subject to treat or prevent a cell proliferative disorder. Such disorders can include, but are not limited to, actinic keratosis, arteriosclerosis, atherosclerosis, bursitis, cirrhosis, hepatitis, mixed connective tissue disease, myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing VATPS or a fragment or derivative thereof may be administered to a subject to treat or prevent a cell proliferative disorder including, but not limited to, those described above.

In a further embodiment, a pharmaceutical composition comprising a substantially purified VATPS in conjunction with a suitable pharmaceutical carrier may be administered to a subject to treat or prevent a cell proliferative disorder including, but not limited to, those provided above.

In still another embodiment, an agonist which modulates the activity of VATPS may be administered to a subject to treat or prevent a cell proliferative disorder including, but not limited to, those listed above.

In a further embodiment, an antagonist of VATPS may be administered to a subject to treat or prevent a cell proliferative disorder. Such a disorder may include, but is not limited to, those discussed above. In one aspect, an antibody which specifically binds VATPS may be used directly as an antagonist or indirectly as a targeting or delivery mechanism for bringing a pharmaceutical agent to cells or tissue which express VATPS.

In an additional embodiment, a vector expressing the complement of the polynucleotide encoding VATPS may be administered to a subject to treat or prevent a cell proliferative disorder including, but not limited to, those described above.

In an additional embodiment, VATPS or a fragment or derivative thereof may be administered to a subject to treat or prevent a neurological disorder. Such a disorder may include, but is not limited to, akathesia, Alzheimer's disease, amnesia, amyotrophic lateral sclerosis, bipolar disorder, catatonia, cerebral neoplasms, dementia, depression, diabetic neuropathy, Down's syndrome, tardive dyskinesia, dystonias, epilepsy, Huntington's disease, peripheral neuropathy, multiple sclerosis, neurofibromatosis, Parkinson's disease, paranoid psychoses, postherpetic neuralgia, schizophrenia, and Tourette's disorder. In one aspect, an antibody which specifically binds VATPS may be used directly as an antagonist or indirectly as a targeting or delivery mechanism for bringing a pharmaceutical agent to cells or tissue which express VATPS.

In another embodiment, a vector capable of expressing VATPS or a fragment or derivative thereof may be administered to a subject to treat or prevent a neurological disorder including, but not limited to, those described above.

In a further embodiment, a pharmaceutical composition comprising a substantially purified VATPS in conjunction with a suitable pharmaceutical carrier may be administered to a subject to treat or prevent a neurological disorder including, but not limited to, those provided above.

In another embodiment, an agonist which modulates the activity of VATPS may be administered to a subject to treat or prevent a neurological disorder including, but not limited to, those listed above.

In a further embodiment, an antagonist of VATPS may be administered to a subject to treat or prevent a neurological disorder. Such a disorder may be, but is not limited to, those discussed above. In one aspect, an antibody which specifically binds VATPS may be used directly as an antagonist or indirectly as a targeting or delivery mechanism for bringing a pharmaceutical agent to cells or tissue which express VATPS.

In an additional embodiment, a vector expressing the complement of the polynucleotide encoding VATPS may be administered to a subject to treat or prevent a neurological disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of VATPS may be produced using methods which are generally known in the art. In particular, purified VATPS may be used to produce antibodies or to screen libraries of pharmaceutical agents to identify those which specifically bind VATPS. Antibodies to VATPS may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with VATPS or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to VATPS have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of VATPS amino acids may be fused with those of another protein, such as KLH, and antibodies to the chimeric molecule may be produced.

Monoclonal antibodies to VATPS may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Nat). Acad. Sci. 81:6851–6855; Neuberger, M. S. et al. (1 984) Nature 312:604–608; and Takeda, S. et al. (1985) Nature 314:452–454.) Alternatively, techniques described for the production of single chain antibodies may be adapted, using methods known in the art, to produce VATPS-specific single chain antibodies. Antibodies with related specificity, but of distinct idiotypic composition, may be generated by chain shuffling from random combinatorial immunoglobulin libraries. (See, e.g., Burton D. R. (1991) Proc. Nat). Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for VATPS may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between VATPS and its specific antibody. A two-site, monoclonal-based immunoassay utilizing monoclonal antibodies reactive to two non-interfering VATPS epitopes is preferred, but a competitive binding assay may also be employed. (Maddox, supra.)

In another embodiment of the invention, the polynucleotides encoding VATPS, or any fragment or complement thereof, may be used for therapeutic purposes. In one aspect, the complement of the polynucleotide encoding VATPS may be used in situations in which it would be desirable to block the transcription of the mRNA. In particular, cells may be transformed with sequences complementary to polynucleotides encoding VATPS. Thus, complementary molecules or fragments may be used to modulate VATPS activity, or to achieve regulation of gene function. Such technology is now well known in the art, and sense or antisense oligonucleotides or larger fragments can be designed from various locations along the coding or control regions of sequences encoding VATPS.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding VATPS. (See, e.g., Sambrook, supra; and Ausubel, supra.)

Genes encoding VATPS can be turned off by transforming a cell or tissue with expression vectors which express high levels of a polynucleotide, or fragment thereof, encoding VATPS. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding VATPS. Oligonucleotides derived from the transcription initiation site, e.g., between about positions –10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding VATPS.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding VATPS. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of VATPS, antibodies to VATPS, and mimetics, agonists, antagonists, or inhibitors of VATPS. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's *Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of VATPS, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example VATPS or fragments thereof, antibodies of VATPS, and agonists, antagonists or inhibitors of VATPS, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of therapeutic to toxic effects is the therapeutic index, and it can be expressed as the $ED_{50}/LD_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind VATPS may be used for the diagnosis of disorders characterized by expression of VATPS, or in assays to monitor patients being treated with VATPS or agonists, antagonists, or inhibitors of VATPS. Antibodies useful for diagnostic purposes may be prepared in the same manner as described above for therapeutics. Diagnostic assays for VATPS include methods which utilize the antibody and a label to detect VATPS in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring VATPS, including ELISAs, RIAs, and FACS, are known in the art and provide a basis for diagnosing altered or abnormal levels of VATPS expression. Normal or standard values for VATPS expression are established by combining body fluids or cell extracts taken from normal mammalian subjects, preferably human, with antibody to VATPS under conditions suitable for complex formation The amount of standard complex formation may be quantitated by various methods, preferably by photometric means. Quantities of VATPS expressed in subject, control, and disease samples from biopsied tissues are compared with the standard values. Deviation between standard and subject values establishes the parameters for diagnosing disease.

In another embodiment of the invention, the polynucleotides encoding VATPS may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of VATPS may be correlated with disease. The diagnostic assay may be used to determine absence, presence, and excess expression of VATPS, and to monitor regulation of VATPS levels during therapeutic intervention.

In one aspect, hybridization with PCR probes which are capable of detecting polynucleotide sequences, including genomic sequences, encoding VATPS or closely related molecules may be used to identify nucleic acid sequences which encode VATPS. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding VATPS, allelic variants, or related sequences.

Probes may also be used for the detection of related sequences, and should preferably have at least 50% sequence identity to any of the VATPS encoding sequences. The hybridization probes of the subject invention may be DNA or RNA and may be derived from the sequence of SEQ ID NO: 3, SEQ ID NO: 4 or from genomic sequences including promoters, enhancers, and introns of the VATPS gene.

Means for producing specific hybridization probes for DNAs encoding VATPS include the cloning of polynucleotide sequences encoding VATPS or VATPS derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as 32p or 35S, or by enzymatic labels, such as alkaline phosphatase coupled to the probe via avidin/biotin coupling systems, and the like.

Polynucleotide sequences encoding VATPS may be used for the diagnosis of a cell proliferative or neurological disorder associated with expression of VATPS. Examples of such disorders include, but are not limited to, actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia; cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and neurological disorders such as akathesia, Alzheimer's disease, amnesia, amyotrophic lateral sclerosis, bipolar disorder, catatonia, cerebral neoplasms, dementia, depression, diabetic neuropathy, Down's syndrome, tardive dyskinesia, dystonias, epilepsy, Huntington's disease, peripheral neuropathy, multiple sclerosis, neurofibromatosis, Parkinson's disease, paranoid psychoses, postherpetic neuralgia, schizophrenia, and Tourette's disorder. The polynucleotide sequences encoding VATPS may be used in Southern or Northern analysis, dot blot, or other membrane-based technologies; in PCR technologies; in dipstick, pin, and ELISA assays; and in microarrays utilizing fluids or tissues from patients to detect altered VATPS expression. Such qualitative or quantitative methods are well known in the art.

In a particular aspect, the nucleotide sequences encoding VATPS may be useful in assays that detect the presence of associated disorders, particularly those mentioned above. The nucleotide sequences encoding VATPS may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding VATPS in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of VATPS, a normal or standard profile for expression is established. This may be accomplished by combining body fluids or cell extracts taken from normal subjects, either animal or human, with a sequence, or a fragment thereof, encoding VATPS, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding VATPS may involve the use of PCR. These oligomers may be chemically synthesized, generated enzymatically, or produced in vitro. Oligomers will preferably contain a fragment of a polynucleotide encoding VATPS, or a fragment of a polynucleotide complementary to the polynucleotide encoding VATPS, and will be employed under optimized conditions for identification of a specific gene or condition. Oligomers may also be employed under less stringent conditions for detection or quantitation of closely related DNA or RNA sequences.

Methods which may also be used to quantitate the expression of VATPS include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251 116; Shalon, D. et al. (1995) PCT application WO95/35505; Heller, R. A. et al. (1997) Proc. Natl. Acad. Sci. 94:2150–2155; and Heller, M. J. et al. (1 997) U.S. Pat. No. 5,605,662.)

In another embodiment of the invention, nucleic acid sequences encoding VATPS may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat Genet. 15:345–355; Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding VATPS on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22-23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, VATPS, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between VATPS and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with VATPS, or fragments thereof, and washed. Bound VATPS is then detected by methods well known in the art. Purified VATPS can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding VATPS specifically compete with a test compound for binding VATPS. In this manner, antibodies can be used to detect the presence of any peptide which shares one or more antigenic determinants with VATPS.

In additional embodiments, the nucleotide sequences which encode VATPS may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. cDNA Library Construction

The HIPONON02 normalized brain library was constructed from 1.13 million independent clones from a hippocampus tissue library. Starting RNA was made from the hippocampus tissue of a 72-year-old Caucasian female, who died from a cerebrovascular accident. The library was oligo (dT)-primed, and cDNAs were cloned directionally into the pSPORT1 vector (Life Technologies) using SalI (5') and NotI (3'). The normalization and hybridization conditions were adapted from Soares et al. (Proc. Natl. Acad. Sci. (1994) 91:9228–9232), except that a significantly longer (48-hour) reannealing hybridization was used.

The TESTTUT02 library was constructed using RNA isolated from a testicular tumor removed from a 31-year-old Caucasian male during unilateral orchiectomy. Pathology indicated embryonal carcinoma forming a largely necrotic mass involving the entire testicle. Rare foci of residual testicle showed intralobular germ cell neoplasia. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte Pharmaceuticals, Palo Alto Calif.).

II. Isolation and Sequencing of cDNA Clones

Plasmids were recovered from host cells by in vivo excision (UniZAP vector system, Stratagene) or by cell lysis. Plasmids were purified using the MAGIC MINI-PREPS DNA purification system (Promega, Madison, Wis.); Miniprep kit (Advanced Genetic Technologies Corporation, Gaithersburg, Md.); QIAwell-8 Plasmid, QIAwell PLUS DNA, or QIAwell ULTRA DNA purification systems; or REAL Prep 96 plasmid kit (QIAGEN Inc) using the recommended protocol. Following precipitation, plasmids were resuspended in 0.1 ml of distilled water and stored, with or without lyophilization, at 4° C.

Alternatively, plasmid DNA was amplified from host cell lysates using direct link PCR (Rao, V. B. (1994) Anal. Biochem. 216:1–14) in a high-throughput format. Host cell lysis and thermal cycling steps were carried out in a single reaction mixture. Samples were processed and stored in 384-well plates (Genetix Ltd, Christchurch UK) and concentration of amplified plasmid DNA was quantified fluorometrically using Pico Green Dye (Molecular Probes, Eugene Oreg.) and a Fluoroscan II fluorescence scanner (Labsystems Oy, Helsinki, Finland).

III. Sequencing and Analysis

The cDNAs were prepared for sequencing using either an ABI Catalyst 800 (Perkin Elmer) or a Hamilton Micro Lab 2200 (Hamilton, Reno, Nev.) in combination with Peltier Thermal Cyclers (PTC200; MJ Research, Watertown Mass.). The cDNAs were sequenced on the ABI 373 or 377 DNA Sequencing systems (Perkin Elmer) by the method of Sanger F and A. R. Coulson (1975; J. Mol. Biol. 94:441–448) using standard ABI protocols, base calling software, and kits. Alternatively, cDNAs were sequenced using solutions and dyes from Amersham Pharmacia Biotech. Reading frame was determined using standard methods (Ausubel, supra).

The cDNA sequences and the full length nucleotide and amino acid sequences disclosed in the Sequence Listing were queried against databases such as GenBank primate (pri), rodent (rod), mammalian (mamp), vertebrate (vrtp), and eukaryote (eukp) databases, SwissProt, BLOCKS, and other databases which contain previously identified and annotated motifs and sequences. Algorithms such as Smith Waterman which deal with primary sequence patterns and secondary structure gap penalties (Smith, T. et al. (1992) Protein Engineering 5:35–51) and programs and algorithms such as BLAST (Basic Local Alignment Search Tool; Altschul, S. F. (1 993) J. Mol. Evol 36:290–300; and Altschul et al. (1990) J. Mol. Biol. 215:403–410), and HMM (Hidden Markov Models; Eddy, S. R. (1996) Cur. Opin. Str. Biol. 6:361–365 and Sonnhammer, E. L. L. et al. (1997) Proteins 28:405–420) were used to assemble and analyze nucleotide and amino acid sequences. The databases, programs, algorithms, methods and tools are available, well known in the art, and described in Ausubel (supra, unit 7.7), in Meyers, R. A. (1995; *Molecular Biology and Biotechnology*, Wiley VCH, Inc, New York N.Y., p 856–853), in documentation provided with software (Genetics Computer Group (GCG), Madison Wis.), and on the world wide web (www). Two comprehensive websites which list, describe, and/or link many of the databases and tools are: 1) the www resource in practical sequence analysis (http://genome.wustl.edu/), and 2) the bibliography of computational gene recognition (http://linkage.rockefeller.edu/wli/gene/programs.html). For example, the first website links PFAM as a database (http://genome.wustl.edu/Pfam/) and as an HMM search tool (http://genome.wustl.edu/eddy/cgi-bin/hmm_page.cgi).

TABLE 1 summarizes the databases and tools used herein. The first column of TABLE 1 shows the tool, program, or algorithm; the second column, the database; the third column, a brief description; and the fourth column (where applicable), scores for determining the strength of a match between two sequences (the higher the value, the more homologous).

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.) Analogous computer techniques applying BLAST were used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or similar.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of Northern analysis are reported as a list of libraries in which the transcript encoding VATPS occurs. Abundance and percent abundance are also reported. Abundance directly reflects the number of times a particular transcript is represented in a cDNA library, and percent abundance is abundance divided by the total number of sequences examined in the cDNA library.

V. Extension of VATPS Encoding Polynucleotides

The nucleic acid sequence of Incyte Clones 2246348 and 2346304 were used to design oligonucleotide primers for extending partial nucleotide sequence to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO™ 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer—primer dimerizations was avoided.

Selected human cDNA libraries (GIBCO BRL) were used to extend the sequence. If more than one extension is necessary or desired, additional sets of primers are designed to further extend the known region.

High fidelity amplification was obtained by following the instructions for the XL-PCR™ kit (Perkin Elmer) and thoroughly mixing the enzyme and reaction mix. PCR was performed using the Peltier Thermal Cycler (PTC200; M. J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 μl to 10 μl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK™ (QIAGEN Inc.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent *E. coli* cells (in 40 μl of appropriate media, were transformed with 3 μl of ligation mixture and cultured in 80 μl of SOC medium. (See, e.g., Sambrook, supra, Appendix A, p. 2.) After incubation for one hour at 37° C., the *E. coli* mixture was plated on Luria Bertani (LB) agar (See, e.g., Sambrook, supra, Appendix A, p. 1) containing carbenicillin (2x carb). The following day, several colonies were randomly picked from each plate and cultured in 150 if of liquid LB/2xcarb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| --- | --- |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO: 3, SEQ ID NO: 4 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO: 3, SEQ ID NO: 4 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO™ 4.06 software (National Biosciences) and labeled by combining 50 pmol of each oligomer, 250 $\mu$Ci of $[\gamma\text{-}^{32}P]$ adenosine triphosphate (Amersham Pharmacia Biotech), and T4 polynucleotide kinase (DuPont NEN®, Boston, Mass.). The labeled oligonucleotides are substantially purified using a Sephadex™ G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, XbaI, or Pvu II (DuPont NEN, Boston, Mass.).

The DNA from each digest is fractionated on a 0.7% agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the VATPS-encoding sequences, or any parts thereof, are used to detect, decrease, or inhibit expression of naturally occurring VATPS. Although use of oligonucleotides comprising from about 15 to 30 base pairs is described, essentially the same procedure is used with smaller or with larger sequence fragments. Appropriate oligonucleotides are designed using OLIGO™ 4.06 software and the coding sequence of VATPS. To inhibit transcription, a complementary oligonucleotide is designed from the most unique 5' sequence and used to prevent promoter binding to the coding sequence. To inhibit translation, a complementary oligonucleotide is designed to prevent ribosomal binding to the VATPS-encoding transcript.

IX. Expression of VATPS

Expression and purification of VATPS is achieved using bacterial or virus-based expression systems. For expression of VATPS in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express VATPS upon induction with isopropyl beta-D-thiogalactopyranoside (IPTG). Expression of VATPS in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding VATPS by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1 994) Proc. Natl. Acad. Sci. USA 91:3224–3227; Sandig, V. et al. (1996) Hum. Gene Ther. 7:1937–1945.)

In most expression systems, VATPS is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from VATPS at specifically engineered sites. FLAG, an 8-amino acid peptide, enables immunoaffinity purification using commercially available monoclonal and polyclonal anti-FLAG antibodies (Eastman Kodak, Rochester, N.Y.). 6-His, a stretch of six consecutive histidine residues, enables purification on metal-chelate resins (QIAGEN Inc, Chatsworth, Calif.). Methods for protein expression and purification are discussed in Ausubel, F. M. et al. (1995 and periodic supplements) *Current Protocols in Molecular Biology*, John Wiley & Sons, New York, N.Y., ch 10, 16. Purified VATPS obtained by these methods can be used directly in the following activity assay.

X. Demonstration of VATPS Activity

The activity of VATPS is demonstrated by the measurement of proton flux in phospholipid vesicles containing vp-ATPase reconstituted from its constituent polypeptides, including VATPS (Zhang, J. et al. (1992) J. Biol. Chem. 267: 9773–78). Reconstituted vp-ATPase is incorporated into phospholipid vesicles. The vesicles are incubated in 20 mM HEPES buffer, pH 7.0, containing 2 $\mu$M 9-amino-6-chloro-2 methoxyacridine (ACMA). Proton flux is initiated by the addition of 20 nM valinomycin, and measured by fluorescence quenching of ACMA in a fluorescence spectrophotometer using excitation and emission wavelengths of 410 nm and 490 nm, respectively. A negative control assay is performed using vp-ATPase reconstituted in the absence of VATPS. A positive control assay is performed using native vp-ATPase assayed in an identical manner. Quenching of ACMA fluorescence in the vp-ATPase assay containing reconstituted VATPS compared to a lack of quenching in the negative control is evidence of VATPS activity. The level of ACMA quenching is proportional to the amount of vp-ATPase and hence VATPS present in the assayed sample.

XI. Functional Assays

VATPS function is assessed by expressing the sequences encoding VATPS at physiologically elevated levels in mammalian cell culture systems. cDNA is subcloned into a mammalian expression vector containing a strong promoter that drives high levels of cDNA expression. Vectors of choice include pCMV SPORT™ (Life Technologies, Gaithersburg, Md.) and pCR™ 3.1 (Invitrogen, Carlsbad, Calif., both of which contain the cytomegalovirus promoter. 5–10 $\mu$g of recombinant vector are transiently transfected into a human cell line, preferably of endothelial or hematopoietic origin, using either liposome formulations or electroporation. 1–2 $\mu$g of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech, Palo Alto, Calif.), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York, N.Y.

The influence of VATPS on gene expression can be assessed using highly purified populations of cells transfected with sequences encoding VATPS and either CD64 or CD64-GFP. CD64 and CD64-GFP are expressed on the surface of transfected cells and bind to conserved regions of human immunoglobulin (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding VATPS and other genes of interest can be analyzed by Northern analysis or microarray techniques.

XII. Production of VATPS Specific Antibodies

VATPS substantially purified using polyacrylamide gel electrophoresis (PAGE)(see, e.g., Harrington, M. G. (1990) Methods Enzymol. 182:488–495), or other purification techniques, is used to immunize rabbits and to produce antibodies using standard protocols.

Alternatively, the VATPS amino acid sequence is analyzed using LASERGENE™ software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring VATPS Using Specific Antibodies

Naturally occurring or recombinant VATPS is substantially purified by immunoaffinity chromatography using antibodies specific for VATPS. An immunoaffinity column is constructed by covalently coupling anti-VATPS antibody to an activated chromatographic resin, such as CNBr-activated Sepharose (Pharmacia & Upjohn). After the coupling, the resin is blocked and washed according to the manufacturer's instructions.

Media containing VATPS are passed over the immunoaffinity column, and the column is washed under conditions that allow the preferential absorbance of VATPS (e.g., high ionic strength buffers in the presence of detergent). The column is eluted under conditions that disrupt antibody-NATPS binding (e.g., a buffer of pH 2 to pH 3, or a high concentration of a chaotrope, such as urea or thiocyanate ion), and VATPS is collected.

XIV. Identification of Molecules Which Interact with VATPS

VATPS, or biologically active fragments thereof, are labeled with 125I Bolton-Hunter reagent. (See, e.g., Bolton et al. (1973) Biochem. J. 133:529.) Candidate molecules previously arrayed in the wells of a multi-well plate are incubated with the labeled VATPS, washed, and any wells with labeled VATPS complex are assayed. Data obtained using different concentrations of VATPS are used to calculate values for the number, affinity, and association of VATPS with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Program/algorithm | Databases | Description | Useful Parameters |
| --- | --- | --- | --- |
| ESTs | | | |
| Smith Waterman | GenBank | Local alignment algorithm for homology searching | min length = 49 nt <12% uncalled bases |
| FASTA | GenBank | Fast nucleotide sequence database searching program for UNIX, VMS | |
| BLAST | GenBank | Ultra-fast database searching program for UNIX, VMS C source | Log likelihood for exact matches is ~$10^{-25}$ and for homologs > $10^{-8}$ |
| Full Length | | | |
| Phred | | Reads trace data from sequencing runs, makes base calls for assembly of cDNA sequences, produces quality scores | |
| Phrap | | Quality-score based assembly program for shotgun sequences | match > 56 score > 120 |
| CONSED | | Graphical tool for editing Phrap contigs | |
| GCG Assembly, Motifs, Profilescan, | GenBank PROSITE | Wisconsing PackagePrograms for the assembly, editing, and characterization of nucleotide sequences | |
| Spscan | | Examines proteins for secretory, signal sequences | >7 strong, 4.5–7 suggestive |
| GENEMARK | | Statistical analysis of nucleotide sequences to identify open reading frame | |
| BLAST | GenBank SwissProt | Ultra-fast database searching program for UNIX, VMS C source | score > 100, P < 1e–5 |
| FASTX | GenBank SwissProt | Fast amino acid sequence database searching program for UNIX, VMS | log likelihood > 17 |
| BLIMPS | BLOCKS PRINTS | Weighted matrix analysis for prediction of protein family | >1300 strong, 1000–1300 suggestive, P < 1c–3 |
| PFAM | PROSITE | Analyses sequences 3–60 amino acids long which correspond to highly conserved regions of a protein family | Score > 11 strong, 8–10 suggestive |
| HMM | | Probabilistic approaches and modeling of the primary structure of protein families | Score > 11 strong, 8–10 suggestive |
| McDNAsis Pro | | Software for sequence analysis | |
| LASERGENE | | Software programs (EditSeq, MegAlign, PrimerSelect, Protean, SeqMan, etc.) for sequence analysis | |

What is claimed is:

1. An isolated and purified polynucleotide comprising a polynucleotide encoding the polypeptide as shown in SEQ ID NO: 1.

2. An isolated and purified polynucleotide having a sequence which is fully complementary to the polynucleotide sequence of claim 1.

3. An isolated and purified polynucleotide comprising the polynucleotide sequence as shown in SEQ ID NO: 3.

4. An isolated and purified polynucleotide having a sequence which is fully complementary to the polynucleotide of claim 3.

5. An expression vector comprising the polynucleotide of claim 1.

6. A host cell comprising the expression vector of claim 5.

7. A method for producing a polypeptide comprising the amino acid sequence as shown in SEQ ID NO: 1, the method comprising the steps of:

a) culturing the host cell of claim 6 under conditions suitable for the expression of the polypeptide; and b) recovering the polypeptide from the host cell culture.

8. A method for detecting a polynucleotide encoding the polypeptide comprising the amino acid sequence as shown in SEQ ID NO: 1, the method comprising the steps of:

(a) hybridizing the polynucleotide of claim 2 to at least one of the nucleic acids in the biological sample, thereby forming a hybridization complex; and (b) detecting the hybridization complex, wherein the presence of the hybridization complex correlates with the presence of the polynucleotide encoding the polypeptide in the biological sample.

9. The method of claim 8 further comprising amplifying the polynucleotide prior to hybridization.

* * * * *

SEQUENCE LISTING (1) GENERAL INFORMATION:

(iii) NUMBER OF SEQUENCES:15

(2) INFORMATION FOR SEQ ID NO:   1:

(i) SEQUENCE CHARACTERISTICS:
      (A) LENGTH: 118 amino acids
      (B) TYPE: amino acid
      (C) STRANDEDNESS: single
      (D) TOPOLOGY: linear (vii) IMMEDIATE SOURCE:
      (A) LIBRARY: HIPONON02
      (B) CLONE: 2246348

(xi) SEQUENCE DESCRIPTION: SEQ ID NO: 1 :

Met Ala Ser Gln Ser Gln Gly Ile Gln Gln Leu Leu Gln Ala Glu
            5                    10                  15

```
Lys Arg Ala Ala Glu Lys Val Ala Asp Ala Arg Lys Arg Lys Ala
                20                  25                  30

Arg Arg Leu Lys Gln Ala Lys Glu Glu Ala Gln Met Glu Val Glu
            35                  40                  45

Gln Tyr Arg Arg Glu Arg His Glu Phe Gln Ser Lys Gln Gln
        50                  55                  60

Ala Ala Met Gly Ser Gln Gly Asn Leu Ser Ala Glu Val Glu Gln
            65                  70                  75

Ala Thr Arg Arg Gln Val Gln Gly Met Gln Ser Ser Gln Gln Arg
            80                  85                  90

Asn Arg Glu Arg Val Leu Ala Gln Leu Leu Gly Met Val Cys Asp
            95                  100                 105

Val Arg Pro Gln Val His Pro Asn Tyr Arg Ile Ser Ala
            110                 115
```

(2) INFORMATION FOR SEQ ID NO:     2:

(i) SEQUENCE CHARACTERISTICS:
        (A) LENGTH: 81 amino acids
        (B) TYPE: amino acid
        (C) STRANDEDNESS: single
        (D) TOPOLOGY: linear (vii) IMMEDIATE SOURCE:
        (A) LIBRARY: TESTTUT02
        (B) CLONE: 2346304

(xi) SEQUENCE DESCRIPTION: SEQ ID NO: 2 :

```
Met Thr Ala His Ser Phe Ala Leu Pro Val Ile Ile Phe Thr Thr
                5                   10                  15

Phe Trp Gly Leu Val Gly Ile Ala Gly Pro Trp Phe Val Pro Lys
            20                  25                  30

Gly Pro Asn Arg Gly Val Ile Ile Thr Met Leu Val Ala Thr Ala
            35                  40                  45

Val Cys Cys Tyr Leu Phe Trp Leu Ile Ala Ile Leu Ala Gln Leu
            50                  55                  60

Asn Pro Leu Phe Gly Pro Gln Leu Lys Asn Glu Thr Ile Trp Tyr
            65                  70                  75

Val Arg Phe Leu Trp Glu
            80
```

(2) INFORMATION FOR SEQ ID NO:     3:

(i) SEQUENCE CHARACTERISTICS:
        (A) LENGTH: 1192 base pairs
        (B) TYPE: nucleic acid
        (C) STRANDEDNESS: single
        (D) TOPOLOGY: linear (vii) IMMEDIATE SOURCE:
        (A) LIBRARY: HIPONON02
        (B) CLONE: 2246348

(xi) SEQUENCE DESCRIPTION: SEQ ID NO: 3 :

```
TGGGAGCCAT CTGGTACTTT GACAGCATTC AAAACAGCAT CGGCCATAAC AACAGAAATG      60

GCCAGTCAGT CCCAAGGTAT CCAGCAGCTT CTGCAAGCTG AGAAGCGGGC AGCTGAGAAG     120

GTGGCAGATG CCAGAAAGAG GAAGGCCCGG CGACTGAAGC AGGCAAAGGA GGAGGCACAG     180

ATGGAGGTGG AGCAATACCG CAGAGAGCGA GAGCACGAAT TCCAGAGCAA GCAGCAGGCG     240

GCCATGGGCT CCCAGGGGAA CCTGTCTGCT GAGGTGGAGC AGGCTACAAG GCGCCAGGTG     300
```

-continued

```
CAGGGCATGC AGAGCTCCCA GCAGAGAAAC CGAGAGCGTG TCCTGGCCCA GCTTCTTGGC      360

ATGGTCTGCG ACGTCAGGCC CCAGGTCCAC CCCAACTACC GGATTTCTGC CTAGGGCCAC      420

CGTAGGGCCT GACTCCTTCT GCCAGTTCCC TCCCTCAAAG AAATCCTCCA ATCAAAATCA      480

CCTCCCACCA TAATCCCTGT CTTCTTTCCA TCCCCTAGAA ATCCTGGGAG GCAGGATCCA      540

ATAATTTTCC TGTGACACTT ATAAATATCC TGCTCACATC TGAATCTCCT TGTTGTTCTT      600

TAACCCTCAC TGGGACTTTG TAAACTTCCA AGTCATTCTC ACCTAAACCC TCTGTGAAAT      660

TTGTAATATG GGGAAGTAGG AATGTGGAAA ACATCCTGAC TTCAGTGTCT GGCCGATGTG      720

GGTCCCTCTC TTGACCCTGT CACTTGCTGG CTGTGAAACC AGGACAAGCT ACTTAACTTG      780

GTAGCCTCGA TGTCCTCCTC TGTGAAACTG GGATGATAAT AATGCCTACC TTGTGAGGGT      840

TGCTTCAATG ATTAGGAATC ATTCTGTAAA GTCTAGCAGA GTTCCTTGCA TGTTGTAGCA      900

GTGATTCAGT AAGTAGCAAC CCTGTGATAC TATTACCACC ACCTGCTCAC TGGTCAAAAC      960

CTACACAGCT GTTTCCTCAC GTCCATCACT GGCTCTCTAA TTCCACTTGT TCATTCTGTG     1020

ACCCTAGTTA TTTTCTGAAA AATTGGTTCT TCTCTTTTCC CAGAGACCTT CTGATCTCCA     1080

AAAAGAGGAG ATGACTACAT TTAGCCCCTC TCTTATAATT CCAGGTAGAT AACTGCATTT     1140

TGTAGCCTCT CTTTGTTTTT CTTTTGCTGA TCTTTGTCTT TATTAGATTT TC             1192
```

(2) INFORMATION FOR SEQ ID NO: 4:

(i) SEQUENCE CHARACTERISTICS:
        (A) LENGTH: 1685 base pairs
        (B) TYPE: nucleic acid
        (C) STRANDEDNESS: single
        (D) TOPOLOGY: linear (vii) IMMEDIATE SOURCE:
        (A) LIBRARY: TESTTUT02
        (B) CLONE: 2346304

(xi) SEQUENCE DESCRIPTION: SEQ ID NO: 4 :

```
CGGCTGGGGA CCCGCGCACC TGCAGCGCCC GCTGCTCGGC CCTGCATCCT GCCTGGGCAT       60

CCTGCGCCCG GCCATGACGG CGCACTCATT CGCCCTCCCG GTCATCATCT TCACCACGTT      120

CTGGGGCCTC GTCGGCATCG CCGGGCCCTG GTTCGTGCCG AAGGGACCCA ACCGCGGAGT      180

GATCATCACC ATGCTGGTCG CCACCGCCGT CTGCTGTTAC CTCTTCTGGC TCATCGCCAT      240

CCTGGCGCAG CTGAACCCCC TGTTCGGGCC CCAGCTGAAG AATGAGACCA TCTGGTACGT      300

GCGCTTCCTG TGGGAGTGAC CCGCCGCCCC CGACCCAGGT GCCCAGCTCT CGGAATGACT      360

GTGGCTCCAC TGTCCCTGAC AACCCCTTCG TCCGGACCCT CCCCCACACA ACTATGTCTG      420

GTCACCAGCT CCCTCCTGCT GGCACCCAGA GACCCGGACC CGCAGGCCTG CCTGGTTCCT      480

GGAAGTCTTC CCAGTCTTCC CAGCCAGCCC GGGCCCTGGG GAGCCCTGGG CACAGCAGCG      540

GCCGAGGGGA TGTCCTGCTC CAATACCCGC ACTGCTCTGG AGTTTGCCCT CTTTCCCAAG      600

GAGATGCTGC TGGGGAGCTG GTATGGGTGG GGTCTTTCCC TTTACAGACG GGGCAGATGC      660

CAGGACTCAG CCCATCCTGA GGAGGACACG TGTCCTCATG GAGAGGGTGC TCCGGCCCAG      720

GCGGGGGAGT CGGTGCCCAG TCAGCAGCTC TGCCACCATC CTGCTGGGAA CTGGGGGGGC      780

CTCTATTGGG TTATAGGCAA GGCCTTTTCT CTGGCATGGA ATTGTTAATT TTCTGACACG      840

TCTAGATGTG AAATTTCTGA AAATGTTGAA GCAGAGAAAC ATTCACACAC AAAAAGCAAC      900

ATAGTCATGT GGGTCCAGAT GGCCTCAGTC CTAGATGTTG GCACCCTTTG CTGTGTCTCC      960

TCAGAGTATC CTGTTCCGCC TCCTGCCACC TGGACCTCCC TCAGTGGATG TCTTCCCTCC     1020
```

-continued

```
CCCGACCCCA GCCTGTCAGT CCGAGCACAG TGCAGGTTTG GCTCTGACTT GGGCCTTTGG    1080

CTGCAGTGGG GGTGGATTTC AGAGCCTCTC ATGGCAGCAT CTAAGTGACC AGAGCTGGGA    1140

TGAGAGAGGG GAAGGGGCAA TGTGAGTGGC GCTATGGGAC GGGCCAGCCC TGCTCCTGAG    1200

CCAGCCCCGC CCTCTGCCCC CTGGCCCTGG GCTCTGTGCT AGGGATGGTG AAGAATGGGG    1260

GCGTGCCAGC CTGGCAGGAG TGGGAAGCAA CACGCAGGGG TCCCGGACCT CTCCAGCCTT    1320

GCCCTCACGC TTATCCGAGC TCCCAGTGTG GTTAGCACAG AGCTCACCCA CCTTGCCTGG    1380

CTCCCAGCTG GGGCCTGTCC TCACTGGTGC TCCAGGGGAA GAAACGACAG CCTCACTTCT    1440

GTATGGACTG CTGATGTGGC CTGCCATCCT GTTCAGCGGG CATTGTCTTT GGAGCAGCAG    1500

GAGAATAGGA TGCCTCTCAC TCACATGCCA GTTCCTGGCT GGCCAGCTGC TCAGGGCTCA    1560

GGCTGGGGCC TCCCATTGAC ATCCTCCCCC TACACTCCCT CTCTGAGCCT CCGTCGCCCC    1620

TCCTGTTGGG TAAGGGTGTT GAGTGTGACT TGTGCTGAAA ACCTGGTTCA TATATAATAA    1680

ATAAA                                                                1685

(2) INFORMATION FOR SEQ ID NO:    5:

(i) SEQUENCE CHARACTERISTICS:
        (A) LENGTH: 654 base pairs
        (B) TYPE: nucleic acid
        (C) STRANDEDNESS: single
        (D) TOPOLOGY: linear (vii) IMMEDIATE SOURCE:
        (A) LIBRARY: BRAITUT12
        (B) CLONE: 1616336T6

(xi) SEQUENCE DESCRIPTION: SEQ ID NO: 5 :

TATTTATTAT ATATGAACCA GGTTTTCAGC ACAAGTCACA CTCAACACCC TTACCCAACA      60

GGAGGGGCGA CGGAGGCTCA GAGAGGGAGT GTAGGGGGAG GATGTCAATG GGAGGCCCCA    120

GCCTGAGCCC TGAGCAGCTG GCCAGCCAGG AACTGGCATG TGAGTGAGAG GCATCCTAGT    180

CTCCTGCTGC TCCAAAGACA ATGCCCGCTG AACAGGATGG CAGGCCACAT CAGCAGTCCA    240

TACAGAAGTG AGGCTGTCGT TTCTTCCCCT GGAGCACCAG TGAGGACAGG CCCCAGCTGG    300

GAGCCAGGCA AGGTGGGTGA GCTCTGTGCT AACCACACTG GGAGCTCGGA TAAGCGTGAG    360

GGCAAGGCTG GAGAGGTCCG GGACCCCTGC GTGTTGCTTC CCACTCCTGC CAGGCTGGCA    420

CGCCCCCATT CTTCACCATC CCTAGCACAG AGCCCAGGGC CAGGGGGCAG AGGGCGGGGC    480

TGGCTCAGGA GCAGGGCTGG CCCGTCCCAT AGCGCCACTC ACATTGCCCC TTCCCCTCTC    540

TCATCCCAGC TCTGGTCACT TAGATGCTGC ATGAGANGCT CTGAAATCAC CCCACTGAGC    600

AAANGCCAAG TCAGAGCAAA CTGCACTGTG CTCGACTACA GCTGGGGTTG GGA           654

(2) INFORMATION FOR SEQ ID NO:    6:

(i) SEQUENCE CHARACTERISTICS:
        (A) LENGTH: 670 base pairs
        (B) TYPE: nucleic acid
        (C) STRANDEDNESS: single
        (D) TOPOLOGY: linear (vii) IMMEDIATE SOURCE:
        (A) LIBRARY: BRSTNOT09
        (B) CLONE: 1661631F6

(xi) SEQUENCE DESCRIPTION: SEQ ID NO: 6 :

GAAACATTCA CACACAAAAA GCAACATAGT CATGTGGGTC CAGATGGCCT CAGTCCTAGA     60

TGTTGGCACC CTTTGCTGTG TCTCCTCAGA GTATCCTGTT CCGCCTCCTG CCACCTGGAC    120
```

```
CTCCCTCAGT GGATGTCTTC CCTCCCCCGA CCCCAGCCTG TCAGTCCGAG CACAGTGCAG      180

GTTTGGCTCT GACTTGGGCC TTTGGCTGCA GTGGGGTGG ATTTCAGAGC CTCTCATGGC       240

AGCATCTAAG TGACCAGAGC TGGGATGANA NANGGGAAGG GGCAATGTGA GTGGCGCTAN      300

GGGANGGGCC ANCCCTGCTC CTGANCCAGT CNCGNAATTT NACCNNTGGC CNTAGGGCNC      360

TGTGCTTAGG GATGGANAAG AATGGGGGGC CTGNNAACCT TTTACAGGAA NTGGTTAAGC      420

AAAAATGGCA ANGGGGTTCC CNGGGNCCCC ANTNAAGCCC NTTAAGNGTN AACCGGTTAA      480

TTNCGGGGGC TNCCCAAATG GGGGGTTTAA CCNAAAAAGG GTTCNCNCCG AANTTTTNNC      540

NTTGGGGGCC CCANAANTGG GGGCCCTTNG NCNTCAANNA GATTCCCCCC AAAGGGGNCC      600

CANAAAGGGN CGGCTTGGAA NTNCTNNAAA NGGGATTGNT TAAAANTNGG CTTTACAANN      660

GCGTTTNAGG                                                             670

(2) INFORMATION FOR SEQ ID NO:    7:

(i) SEQUENCE CHARACTERISTICS:
        (A) LENGTH: 543 base pairs
        (B) TYPE: nucleic acid
        (C) STRANDEDNESS: single
        (D) TOPOLOGY: linear (vii) IMMEDIATE SOURCE:
        (A) LIBRARY: PROSTUT12
        (B) CLONE: 1811952F6

(xi) SEQUENCE DESCRIPTION: SEQ ID NO: 7 :

CCCTTCGTCC GGACCCTCCC CCACACAACT ATGTCTGGTC ACCAGCTCCC TCCTGCTGGC       60

ACCCAGAGAC CCGGACCCGC AGGCCTGCCT GGTTCCTGGA AGTCTTCCCA GTCTTCCCAG      120

CCAGCCCGGG CCCTGGGGAG CCCTGGGCAC AGCAGCGGCC GAGGGGATGT CCTGCTCCAA      180

TACCCGCACT GCTCTGGAGT TTGCCCTCTT TCCCAAGGAG ATGCTGCTGG GGAGCTGGTA      240

TGGGTGGGGT CTTTCCCTTT ACAGACGGGG CAGATGCCAG GACTCAGCCC ATCCTGAGGA      300

GGACACGTGT CCTCATGGAG AGGGTGCTCC GGCCCAGGCG GGGGAGTCGG TGCCCAGTCA      360

GCAGCTCTGC CANCATCCTG CTGGGAACTG GGGGGGCCTC TATTGGGTTA TAGGCAAGGC      420

TTTTCTCTGG CATGGAATGT TAATTTTCTG ACACGTCTAG ATGTGAAATT TCTGAAAATG      480

TTGAAGCAGA GAAACATTCA CACACAAAAA GAACATAGTC ATGTGGGTCC AATGGCTCAG      540

TCT                                                                    543

(2) INFORMATION FOR SEQ ID NO:    8:

(i) SEQUENCE CHARACTERISTICS:
        (A) LENGTH: 619 base pairs
        (B) TYPE: nucleic acid
        (C) STRANDEDNESS: single
        (D) TOPOLOGY: linear (vii) IMMEDIATE SOURCE:
        (A) LIBRARY: BRAINOT09
        (B) CLONE: 2155351T6

(xi) SEQUENCE DESCRIPTION: SEQ ID NO: 8 :

ATTATTTATT ATATATGAAC TAGGTTTTCA GCACAAGTCA CACTCAACAC CCTTACCCAA       60

CAGGAGGGGC GACGGAGGCT CAGAGAGGGA GTGTAGGGGG AGGATGTCAA TGGGAGGCCC      120

CAGCCTGAGC CCTGAGCAGC TGGCCAGCCA GGAACTGGCA TTGTGAGTGA GAGGCATCCT      180

ATTCTCCTGC TGCTCCAAAG ACAATGCCCG CTGAACAGGA TGGCAGGCCA CATCAGCAGT      240
```

-continued

```
CCATACAGAA GTGAGGCTGT CGTTTCTTCC CCTGGAGCAC CAGTGAGGAC AGGCCCCAGC      300

TGGGAGCCAG GCAAGGTGGG TGAGCTCTGT GCTAACCACA CTGGGAGCTC GGGTAAGCGT      360

GAGGGCAAGG CTGGAGAGGT CCGGGACCCC TGCGTGTTGC TTCCCACTCC TGCCAGGCTG      420

GCACGCCCCC ATTCTTCACC ATCCCTAGCA CAGAGCCCAG GGCCAGGGGG CAGAGGGCGG      480

GGCTGGCTCA GGAACAGGGC TGGCCCGTCC CATAGCGCCA CTCACATTGC CCCTTCCCCT      540

CTCTCATCCC AGCTCTGGTC ACTTAGATGC TGCATGAGAG GCTTTNAATC CAACCCCACT      600

GAGCAAAAGC CAAGTAGAG                                                   619
```

(2) INFORMATION FOR SEQ ID NO: 9:

(i) SEQUENCE CHARACTERISTICS:
        (A) LENGTH: 251 base pairs
        (B) TYPE: nucleic acid
        (C) STRANDEDNESS: single
        (D) TOPOLOGY: linear (vii) IMMEDIATE SOURCE:
        (A) LIBRARY: HIPONON02
        (B) CLONE: 2246348CT1

(xi) SEQUENCE DESCRIPTION: SEQ ID NO: 9 :

```
CNTGCTCACT GGTCAAAACC TACACAGCTG TTTCCTNACG TCCATCACTG GCTCTCTAAT       60

TCCACTTGTT CATTCTGTGA CCCTAGTTAT TTTCTGAAAA ATTGGTTCTT CTCTTTTCCC      120

AGAGACCTTC TGATCTCCAA AAAGAGGAGA TGACTACATT TAGCCCCTCT CTTATAATTC      180

CAGGTAGATA ACTGCATTTT GTAGCCTCTC TTTGTTTTTC TTTTGCTGAT CTTTGTCTTT      240

ATTAGATTTT C                                                           251
```

(2) INFORMATION FOR SEQ ID NO: 10:

(i) SEQUENCE CHARACTERISTICS:
        (A) LENGTH: 235 base pairs
        (B) TYPE: nucleic acid
        (C) STRANDEDNESS: single
        (D) TOPOLOGY: linear (vii) IMMEDIATE SOURCE:
        (A) LIBRARY: TESTTUT02
        (B) CLONE: 2346304H1

(xi) SEQUENCE DESCRIPTION: SEQ ID NO: 10 :

```
CGCTGCCCGG CTGGGACCC GCGCACCTGC AGCGCCCGCT GCTCGGCCCT GCATCCTGCC       60

TGGGCATCCT GCGCCCGGCC ATGACGGCGC ACTCATTCGC CCTCCCGGTC ATCATCTTCA      120

CCACGTTCTG GGGCCTCGTC GGCATCGCCG GGCCCTGGTT CGTGCCGAAG GGACCCAACC      180

GCGGAGTGAT CATCACCATG CTGGTCGCCA CCGCCGTCTG CTGTTACTCT TCTGG          235
```

(2) INFORMATION FOR SEQ ID NO: 11:

(i) SEQUENCE CHARACTERISTICS:
        (A) LENGTH: 222 base pairs
        (B) TYPE: nucleic acid
        (C) STRANDEDNESS: single
        (D) TOPOLOGY: linear (vii) IMMEDIATE SOURCE:
        (A) LIBRARY: SMCANOT01
        (B) CLONE: 2481208H1

(xi) SEQUENCE DESCRIPTION: SEQ ID NO: 11 :

```
GCGCGCTGCC CGGCTGGGGA CCCGCGCACC TGCAGCGCCC GCTGCTCGGC CCTGCATCCT      60

GCCTGGGCAT CCTGCGCCCG GCCATGACGG CGCACTCATT CGCCCTCCCG GTCATCATCT     120

TCACCACGTT CTGGGGCCTC GTCGGCATCG CCGGGCCCTG GTTCGTGCCG AAGGGACCCA     180

ACCGCGGAGT GATCATCACC ATGCTGGTCG CCACCGCCGT CT                        222
```

(2) INFORMATION FOR SEQ ID NO: 12:

(i) SEQUENCE CHARACTERISTICS:
        (A) LENGTH: 548 base pairs
        (B) TYPE: nucleic acid
        (C) STRANDEDNESS: single
        (D) TOPOLOGY: linear (vii) IMMEDIATE SOURCE:
        (A) LIBRARY: BRSTTUT15
        (B) CLONE: 3110132F6

(xi) SEQUENCE DESCRIPTION: SEQ ID NO: 12 :

```
GAAGAATGAG ACCATCTGGG CAGGCCTCGG TCATATTATT TTGGATGCGG CCAACCCAGC      60

AGATGGCAGG GCCTGTGTTC CCAGGGTGAC GAGGGGCCCA GGGAGCCATC ACACTCCGG      120

CAGGCACATG GGCTCCCTCC TGCTGGCACC CAGAGACCCG GACCCGCAGG CCTGCCTGGT     180

TCCTGGAAGT CTTCCCAGTC TTCCCAGCCA GCCCGGGCCC TGGGGAGCCC TGGGCACAGC     240

AGCGGCCGAG GGGATGTCCT GCTCCAATAC CCGCACTGCT CTGGAGTTTG CCCTCTTTCC     300

CAAGGAGATG CTGCTGGGGA GCTGAGTATC CTGTTCCGCC TCCTGCCACC TGGACCTCCC     360

TCAGTGGATG TCTTCCCTCC CCCGACCCCA GCCTGTCAGT CCGAGCACAG TGCAGTGGGG     420

CCTGTNCTCA CTGGTGCTCC AGGGGAAGAA ACGACAGCCT CACTTCTGTA TGGACTGCTG     480

ATGTGGCCTG CATCCTGTTC AGCGGGCATT GTCTTTGGAG CAGCAGGNGA ATAAGGATGC     540

TCTCACTC                                                             548
```

(2) INFORMATION FOR SEQ ID NO: 13:

(i) SEQUENCE CHARACTERISTICS:
        (A) LENGTH: 267 base pairs
        (B) TYPE: nucleic acid
        (C) STRANDEDNESS: single
        (D) TOPOLOGY: linear (vii) IMMEDIATE SOURCE:
        (A) LIBRARY: BRAINOT03
        (B) CLONE: 659609H1

(xi) SEQUENCE DESCRIPTION: SEQ ID NO: 13 :

```
GGGGTGGGAG CCATNTGGTA CTTTGACAGC ATTNAAAACA GCATNGGCCA TAACAACAGA      60

AATGGCCAGT NAGTCCCAAG GTATNCAGCA GNTTCTGCAA GNTGAGAAGC GGGCAGCTGA     120

GAAGGTGGCA GATGCCAGAA AGAGGAAGGC CCGGCGACTN AAGCAGGCAA AGGAGGAGGC     180

ACAGATGGAG GTGGAGCAAT ACCGCAGAGA GCGAGAGNAC GGATTTCAGA GNAAGCAGCA     240

GGNGGNCATG GGGTTCCAGG GGAACCT                                        267
```

(2) INFORMATION FOR SEQ ID NO: 14:

(i) SEQUENCE CHARACTERISTICS:
        (A) LENGTH: 118 amino acids
        (B) TYPE: amino acid
        (C) STRANDEDNESS: single
        (D) TOPOLOGY: linear -continued

```
    (vii) IMMEDIATE SOURCE:
          (A) LIBRARY: GenBank
          (B) CLONE: g1699359

(xi) SEQUENCE DESCRIPTION: SEQ ID NO: 14 :

Met Ala Ser Gln Ser Gln Gly Ile Gln Gln Leu Leu Gln Ala Glu
                  5                  10                  15

Lys Arg Ala Ala Glu Lys Val Ser Glu Ala Arg Lys Arg Lys Asn
             20                  25                  30

Arg Arg Leu Lys Gln Ala Lys Glu Glu Ala Gln Ala Glu Val Glu
             35                  40                  45

Gln Tyr Arg Leu Gln Arg Glu Lys Glu Phe Lys Ala Lys Glu Ala
             50                  55                  60

Ala Ala Leu Gly Ser His Gly Ser Cys Ser Thr Glu Val Glu Lys
             65                  70                  75

Asp Thr Gln Glu Lys Met Thr Ile Leu Gln Thr Tyr Phe Gln Gln
             80                  85                  90

Asn Arg Asp Glu Val Leu Asp Asn Leu Leu Ala Phe Val Cys Asp
             95                 100                 105

Ile Arg Pro Glu Ile His Glu Asn Tyr Arg Ile Asn Gly
            110                 115

(2) INFORMATION FOR SEQ ID NO:     15:

(i) SEQUENCE CHARACTERISTICS:
          (A) LENGTH: 81 amino acids
          (B) TYPE: amino acid
          (C) STRANDEDNESS: single
          (D) TOPOLOGY: linear (vii) IMMEDIATE SOURCE:
          (A) LIBRARY: GenBank
          (B) CLONE: g2584789

(xi) SEQUENCE DESCRIPTION: SEQ ID NO: 15 :

Met Ala Tyr His Gly Leu Thr Val Pro Leu Ile Val Met Ser Val
                  5                  10                  15

Phe Trp Gly Phe Val Gly Phe Leu Val Pro Trp Phe Ile Pro Lys
             20                  25                  30

Gly Pro Asn Arg Gly Val Ile Ile Thr Met Leu Val Thr Cys Ser
             35                  40                  45

Val Cys Cys Tyr Leu Phe Trp Leu Ile Ala Ile Leu Ala Gln Leu
             50                  55                  60

Asn Pro Leu Phe Gly Pro Gln Leu Lys Asn Glu Thr Ile Trp Tyr
             65                  70                  75

Leu Lys Tyr His Trp Pro
             80
```